United States Patent [19]

Markle et al.

[11] Patent Number: 5,596,988

[45] Date of Patent: Jan. 28, 1997

[54] MULTI-PARAMETER SENSOR APPARATUS

[75] Inventors: David R. Markle, Paoli, Pa.; Barry C. Crane, Aston Clinton, England; Michael P. Irvine, Watlington, England; Stuart P. Hendry, Aylesbury, England; William Paterson, High Wycombe, England

[73] Assignee: Biomedical Sensors, Ltd., High Wycombe, England

[21] Appl. No.: 352,340

[22] Filed: Dec. 7, 1994

Related U.S. Application Data

[62] Division of Ser. No. 85,844, Jun. 30, 1993, abandoned.

[51] Int. Cl.⁶ ........................................................ A61B 5/05
[52] U.S. Cl. .......................... 128/635; 128/632; 128/634; 128/637; 128/642; 204/416
[58] Field of Search .................. 128/635–637, 128/639, 642, 632, 634; 204/403, 414, 415, 416

[56] References Cited

U.S. PATENT DOCUMENTS

| | | |
|---|---|---|
| Re. 31,879 | 5/1985 | Lubbers et al. . |
| 3,905,888 | 9/1975 | Mindt et al. . |
| 4,200,110 | 4/1980 | Peterson et al. . |
| 4,568,444 | 2/1986 | Nakamura et al. ............ 128/635 |
| 4,703,756 | 11/1987 | Gough et al. ................. 128/635 |
| 4,727,730 | 3/1988 | Boiarski et al. . |
| 4,854,321 | 8/1989 | Boiarski . |
| 4,889,407 | 12/1989 | Markle et al. .............. 350/96.29 |
| 4,906,232 | 3/1990 | Reynolds . |
| 4,943,364 | 7/1990 | Koch et al. . |
| 4,960,412 | 10/1990 | Fink . |
| 4,966,597 | 10/1990 | Cosman ....................... 128/736 |

FOREIGN PATENT DOCUMENTS 9219150   11/1992   WIPO ........................ 128/635

Primary Examiner—Angela D. Sykes
Assistant Examiner—Bryan K. Yarnell
Attorney, Agent, or Firm—Peter C. Richardson; Lawrence C. Akers; Mark Dryer

[57] ABSTRACT

A multi-parameter catheter comprising sensors enveloped in a sheath made from a biphasic material comprising a layer of microporous hydrophobic substance having micropores which are filled with a hydrophilic substance which when hydrated forms a gel and allows the passage of water-bound ions, and an apparatus for introducing the catheter into a patient's blood vessel.

8 Claims, 5 Drawing Sheets

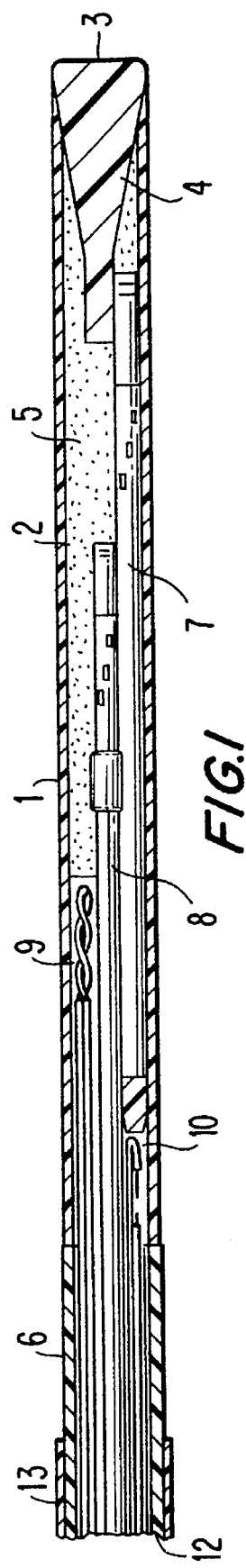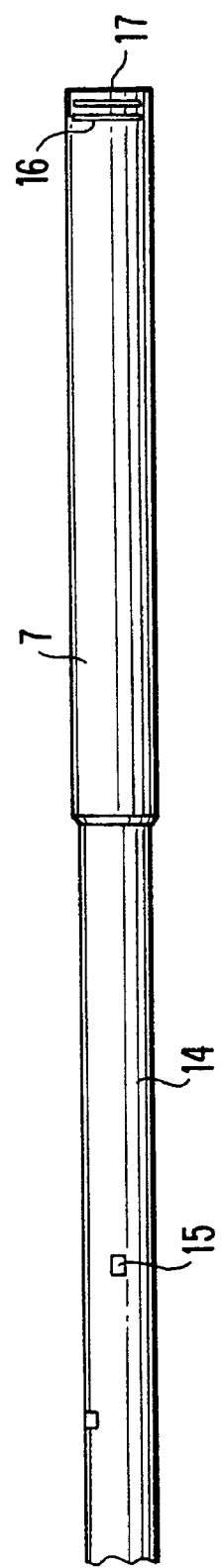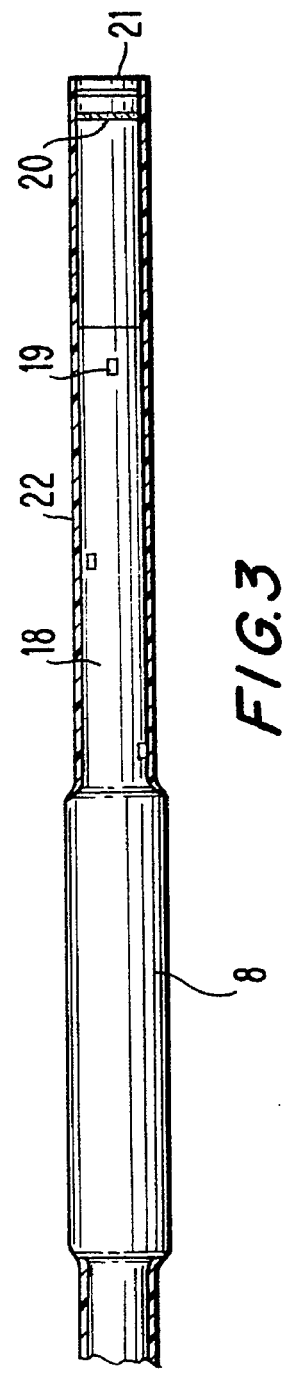

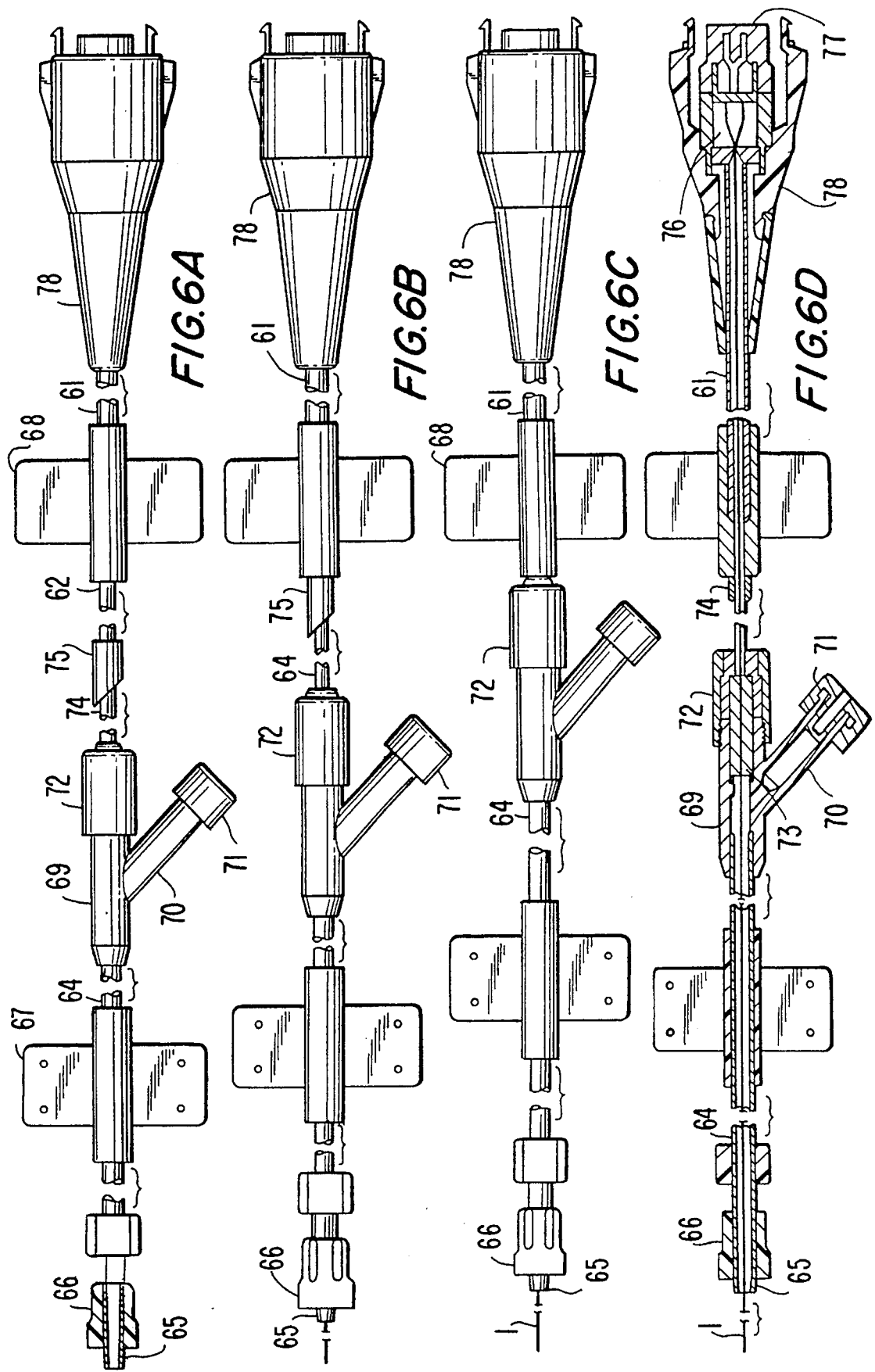

MULTI-PARAMETER SENSOR APPARATUS

This is a division of application Ser. No. 08/085,844, filed on Jun. 30, 1993, now abandoned.

FIELD OF INVENTION

This invention relates to a material which exhibits both hydrophobic and hydrophilic characteristics, defined herein as a "bipbasic" material. More particularly, the invention relates to a biphasic material in the form of a flat or tubular membrane, hereinafter referred to as a biphasic membrane. The invention is also concerned with a catheter containing multi-parameter sensors, herein designated a multi-parameter catheter, having an outer wall at least part of which is made from a biphasic membrane; an apparatus comprising such a catheter in combination with a device for introducing the catheter into a patient's blood vessel and a vacuum rig apparatus for introducing a liquid into a desired space.

BACKGROUND OF THE INVENTION

Invasive sensors for determining the concentration of various analytes in body fluids, particularly the concentration of gasses such as oxygen and carbon dioxide in blood, have been proposed in the art.

U.S. Pat. No. 3,905,888 discloses an electrochemical sensor for determining the oxygen partial pressure in a biological medium comprising a flexible plastic tube which is permeable to oxygen and houses a pair of electrodes surrounded by an electrolyte.

Sensors for the determination of pH and $pCO_2$ normally comprise one or more optical fibers in association with a suitable indicator for the parameter under investigation.

U.S. Pat. No. 4,200,110 discloses a fiber optic probe which includes an ion permeable membrane envelope which encloses the end of a pair of optical fibers. The operation of the probe depends upon the optical detection of a change in color of a pH sensitive dye. U.S. Pat. No. 4,943,364 discloses a fiber-optic probe for measuring the partial pressure of carbon dioxide in a medium comprising a hydrolyzed dye/gel polymer in contact with a bicarbonate solution enveloped in a membrane covering the distal end of the fiber.

U.S. Reissue Pat. No. Re 31,879 discloses a method for measuring the concentration of an analyte in a sample which involves measuring a change in the color characterization of a fluorescent indicator attached to an optical fiber, without or with a gas-permeable membrane.

Commonly assigned U.S. Pat. No. 4,889,407 discloses an optical waveguide sensor for determining an analyte in a medium, which sensor comprises an optical waveguide having a plurality of cells arranged in an array which substantially covers the cross-sectional area of the waveguide, each of said cells containing an indicator sensitive to said analyte.

When a probe, such as one of those disclosed in the above prior art, is used invasively, it is usually introduced into a body lumen, for example a blood vessel, with the aid of an introducer and, to protect the probe itself, avoid contamination, maintain sterility and also facilitate introduction, the probe is usually accommodated within an elongated tubular catheter.

The prior art patents mentioned above disclose sensors adapted to determine a single analyte. However, there is a need in the art for a single device which is capable of determining and monitoring a number of blood parameters, for example, pH, $pO_2$, $pCO_2$ and temperature, and which has a small enough diameter to be inserted into a blood vessel.

U.S. Pat. No. 4,727,730 discloses a blood pressure monitoring apparatus comprising a single fiber probe that interrogates three dye wells each using a fluorescent dye. Blood pressure is monitored with the aid of a diffraction grating.

U.S. Pat. No. 4,854,321 discloses a single probe having multiple dye wells for monitoring blood gases.

U.S. Pat. No. 4,279,795 discloses a hydrophilic-hydrophobic graft copolymer formed by the copolymerization of a free radical polymerizable vinyl monomer capable of forming a hydrophilic polymer and a hydrophobic macromolecular compound.

By using a biphasic membrane as described and claimed herein, it is possible to incorporate sensors for the determination and monitoring of pH, $pO_2$, $pCO_2$ and temperature in a single multi parameter catheter which is narrow enough to be inserted safely into a patient's blood vessel.

Since it is important to avoid contamination and direct operator contact when introducing the catheter into a patient's blood vessel, the invention also provides a device, or introducer, for said introduction.

U.S. Pat. No. 4,906,232 discloses an intravascular delivery device comprising seal means, a delivery assembly having an inner sleeve and stop means.

U.S. Pat. No. 4,960,412 discloses a valve assembly for a catheter introducer.

It has now been found that optimum results are obtained from a multi-parameter catheter if at least part of the tubular wall or outer sheath of the catheter is made from a biphasic membrane as disclosed herein.

SUMMARY OF THE INVENTION

In accordance with the present invention there is provided a biphasic material comprising a layer of microporous hydrophobic substance having micropores which are filled with a hydrophilic substance which when hydrated forms a gel and allows the passage of water-bound ions.

In a preferred embodiment, the layer of microporous hydrophobic substance is a membrane made from a hydrophobic polymer, for example polyethylene, which may be flat or tubular. The substance allows the passage of gasses but, because of its hydrophobicity, the passage of liquid water bound molecules or ions is not possible. Since hydrogen ions require liquid water molecules for transport, the membrane is also impermeable to hydrogen ions. To make the microporous membrane permeable to hydrogen ions, the micropores, a typical size for which is 0.1 micron, are filled with a hydrophilic substance, for example a polyacrylamide, which when hydrated forms a gel and allows the passage of water-bound ions. Thus the membrane is biphasic, i.e. both hydrophobic and hydrophilic.

Due to their high water content, many hydrogels are inherently biocompatable. Also, a hydrogel provides a medium which is permeable to low molecular weight molecules, ions, and gases; although it inhibits the transfer of high molecular weight blood components, which would interfere with the performance of sensors. This combination of properties make a hydrogel satisfactory for use in invasive sensors, particularly pH sensors. However, in general, hydrogels are mechanically weak. This latter disadvantage is overcome by the present invention wherein a preferred hydrogel is incorporated into a microporous layer of substance having the desired mechanical strength to be used as the outer sheath or wall of an invasive catheter. The hydrogel fills the micropores of the microporous layer.

The preferred substance for the microporous layer is high density polyethylene, which is a hydrophobic substance. Another substance which may be used for the microporous layer is polypropylene.

A preferred use for the biphasic membrane of the present invention is as the outer wall of a catheter containing multi-parameter sensors as described hereinafter.

Accordingly, the invention also provides a multi-parameter catheter for the in vivo determination of multiple parameters in a patient's blood comprising an elongated tube with a distal hollow chamber terminating in a distal end, the wall of said chamber being defined at least in part by a biphasic membrane made from a layer of microporous hydrophobic substance having micropores which are filled with a hydrophilic substance which when hydrated forms a gel which allows the passage of water-bound ions and said chamber containing a plurality of sensors mounted sequentially from said distal end within a hydrophilic medium.

In a preferred embodiment of the catheter the sequentially mounted sensors comprise, in sequence from the distal end of the chamber, an optical fiber Ph sensor, an optical fiber $pCO_2$ sensor, a thermocouple temperature sensor and a $pO_2$ sensor. The $pO_2$ sensor may be an electrochemical $pO_2$ sensor as described herein or a fluorescent $pO_2$ sensor.

Preferably the biphasic membrane is a microporous polyethylene tube having micropores which are filled with a polyacrylamide hydrogel, the hydrophilic medium within which the sensors are mounted is a polyacrylamide hydrogel and the distal end of the chamber is sealed by a solid plug made from a thermoplastic polymer.

The invention also provides an apparatus for the in vivo determination of multiple parameters in a patient's blood comprising, in combination, a catheter as described above and a device for introducing the catheter into a patient's blood vessel, which device comprises a first elongated flexible hollow tube having a distal end, a proximal end and a distal portion terminating in said distal end, a second elongated extension tube concentrically mounted within the distal portion of the first tube for telescopic extension beyond the distal end of the first tube and retraction within the first tube, so that when the second tube is fully extended it completely envelopes the catheter and when it is retracted the catheter is exposed, the device also including locking means for locking the second tube in the extended or retracted position as desired, and means for introducing a sterile liquid within said second tube to surround the catheter when it is within the tube.

In the above apparatus the introducer device preferably has a connector at the proximal end thereof, which connector is attached to leads from each sensor of the catheter. The connector is adapted to form a junction with another connector attached to a suitable monitor for monitoring the parameters under investigation by the sensors. Preferably the junction formed by the connectors is protected by a barrier as described and claimed in commonly assigned U.S. Pat. No. 5,230,031.

The invention further provides a vacuum rig apparatus for introducing a liquid into a space defined by a shaped article, which apparatus comprises a series of interconnected vessels attached through a port to a vacuum line, the vessels comprising a first vessel connected to a second vessel, which second vessel is adapted to hold said shaped article and is a hollow tube with a proximal end and a distal end, said distal end being integral with a "U" shaped tube having an open distal end which projects into a space defined by a third vessel which is a reservoir for liquid and has a distal end with a first port and a second port, said first port providing a drain adapted to be plugged or opened as desired and said second port connected to a fourth vessel having first and second sealable ports and a third port for connecting the apparatus to a vacuum line and a tubular conduit connecting the second vessel, from a port adjacent the proximal end thereof, to the fourth vessel, so that said conduit, second vessel, "U" shaped tube, third vessel and fourth vessel form a closed circuit, the apparatus being tiltable about a point midway along the second vessel so that liquid in the reservoir initially at a level below the end of the "U" shaped tube flows into and along the "U" shaped tube into the second vessel to surround the shaped article and fill the space therein when a vacuum is applied to the apparatus.

Preferably, the connection between the first vessel and the second vessel is a tubular conduit which provides a releasable fluid-tight connection from a port in the first vessel to a port at the proximal end of the second vessel.

The vessels of the vacuum rig apparatus have transparent walls which may be made of glass or a transparent plastic.

In a preferred embodiment of the apparatus the tubular second vessel is perpendicular to the third vessel which also is preferably tubular in shape; and the tubular conduit connecting the second vessel to the fourth vessel is preferably diagonal with respect to the third vessel.

The vacuum rig apparatus may be used for filling a chamber of a multi-parameter catheter with a hydrophilic medium in which case the "shaped article" is the tubular chamber which houses the sensors of the catheter and the space defined thereby is the space surrounding the sensors, and the liquid in the reservoir is a hydrogel-forming liquid. The apparatus also may be used for filling the cells in an optical fiber pH sensor or $pCO_2$ sensor; and for introducing the electrolyte into an electrochemical $pO_2$ sensor.

The vacuum rig apparatus additionally may be used to introduce a hydrophilic substance into the micropores of a microporous substrate to form a biphasic membrane according to the invention.

Accordingly the invention still further provides a method for introducing a liquid into a space defined by a shaped article which comprises placing the shaped article in a vessel which is part of a vacuum rig apparatus comprising a liquid reservoir perpendicular to the vessel, introducing liquid into the reservoir, applying a vacuum to the vessel to evacuate gas from the space, tilting the apparatus so that liquid from the reservoir enters the vessel and fills the space.

BRIEF DESCRIPTION OF THE DRAWINGS

The invention will be more particularly described with reference to preferred embodiments illustrated in the accompanying drawings, in which:

FIG. 1 is a schematic side view, partly in cross-section, of a multi-parameter catheter having an outer sheath embodying a biphasic membrane made from the biphasic material according to the invention;

FIG. 2 is an enlarged side view of a pH sensor included in the catheter of FIG. 1;

FIG. 3 is an enlarged side view of a $pCO_2$ sensor included in the catheter of FIG. 1;

FIGS. 6A–6D are enlarged views of the device of FIG. 6 showing the features thereof in more detail;

DETAILED DESCRIPTION OF THE INVENTION

Figure 4:
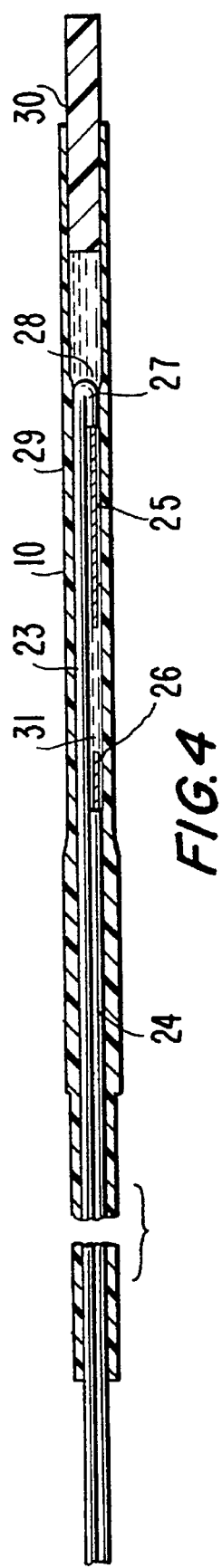
FIG. 4 is an enlarged side view of an electrochemical $pO_2$ sensor included in the catheter of FIG. 1.

A particularly preferred embodiment which utilizes a biphasic membrane according to the present invention is a system for determining certain parameters in the blood of a patient. The parameters are determined by various sensor devices incorporated in a single catheter which is adapted to be inserted into the bloodstream of the patient and, for convenience, the system is designated herein as a multi-parameter catheter system. The biphasic membrane of the invention is used to form at least a part of the tubular wall or outer sheath which envelopes the sensors in the catheter. A device for introducing the catheter into a patient's blood vessel is also described.

Commonly assigned U.S. Pat. No. 4,889,4907, acknowledged above, describes and claims an optical waveguide sensor for determining an analyte in a medium, for example, blood, which sensor comprises an optical waveguide, preferably an optical fiber, having a portion to be brought into contact with said medium, said portion having a plurality of cells arranged in an array which substantially covers the cross-sectional area of the fiber, each of the cells containing an indicator sensitive to the analyte. This sensor is particularly suitable for the determination of pH and $pCO_2$ in blood, and, preferably, a sensor as described and claimed in U.S. Pat. No. 4,889,407 is incorporated in the multi parameter catheter system utilizing the biphasic membrane of the present invention.

FIG. 1 of the accompanying drawings illustrates a multi-parameter catheter 1 comprising a hollow tube defined by a distal portion sheath 2 terminating in a distal end 3 which is sealed by a thermoplastic polymer plug 4 to form a closed chamber 5. The preferred method for sealing the tube with a thermoplastic polymer plug and the resulting tubular assembly is described and claimed in commonly assigned U.S. patent application Ser. No. 887,993 (U.S. Pat. No. 5,280,130). The proximal portion wall 6 of the tube is made from solid non-porous polymeric tubing, for example, polyethylene tubing, and the distal end thereof forms a butt-joint with the sheath 2.

The sheath 2 is a biphasic membrane comprising a layer of a microporous hydrophobic substance the micropores of which are filled with a hydrophilic hydrogel. Also, since the sheath portion of the catheter will be in contact with body fluids, particularly blood, when the catheter is in use, preferably heparin is covalently bound to the outer surface thereof to prevent blood clots.

Preferably the microporous substance is a high density polyethylene and the sheath is a microporous polyethylene hollow fiber (MPHF) with an internal diameter of from about 425 to 475 microns, a maximum external diameter of about 500 microns, and a porosity of about 40%. The preferred hydrophilic substance which fills the micropores of the MPHF is a polyacrylamide hydrogel. The method of filling the micropores with the hydrogel is described hereinafter.

Mounted within the tube, in sequence from the distal end are four sensors, a pH sensor 7, a $pCO_2$ sensor 8, a temperature sensor 9, and a $pO_2$ sensor 10. The sensors are mounted in the desired staggered relationship primarily to reduce the diameter of the catheter. This is because the distal end or tip of each sensor is flared, even though the flare is not immediately apparent at the scale shown in the drawings, and adjacent side-by-side alignment would result in an unacceptable increase in diameter at the tips of the sensors. Also, in the case of the pH and $pCO_2$ sensors, it is desirable to stagger the positioning of the cells in the optical fibers to avoid possible interference of signals.

The preferred staggered sequence of sensors is illustrated in FIG. 1; but other sequences are also possible for operable sensors.

Within the chamber 5 the sensors are surrounded by a hydrophilic medium, preferably a polyacrylate hydrogel containing phenol red indicator. A similar polyacrylate/phenol red hydrogel is impregnated into the cells of the pH sensor.

If desired the sensors may be secured within the catheter by an adhesive plug (not shown).

To reduce interference or noise from extraneous radiation the proximal portion of the catheter is back-filled with a radiation-opaque coating 12, for example of carbon black, the distal end of the opaque coating being adjacent to the distal end of the solid polyethylene tubing 6. Preferably, the catheter is coated by applying a suspension of carbon black in silicone, previously de-gassed, through a syringe in a manner known in the art. The coating is cured by heating in an oven at 40° C. for about 2 hours. Curing is conducted at the sensor end first to prevent tracking of carbon black into the sensors. Alternatively, the coating may be an UV-curing silicone rubber containing carbon black and the curing is conducted at a suitable UV intensity.

The portion of the catheter proximal to the portion containing the sensors has an outer sheath of polyethylene tubing 13.

The individual sensors are illustrated in more detail in the enlarged views of FIGS. 2–5.

FIG. 2 illustrates a preferred pH sensor 7 which comprises an optical fiber 14 having a helical array of cells 15 which substantially covers the cross-sectional area of the fiber. The number of cells in the array may vary up to any desired maximum. Preferably the pH sensor of the invention contains five cells. Each of the cells contains a pH sensitive indicator, preferably phenol red in a gel. The filling of the cells is accomplished by use of a vacuum rig apparatus as described herein. This type of sensor is described and claimed in U.S. Pat. No. 4,899,407. Optical radiation transmitted along the fiber is reflected by a mirror 16 embedded close to the distal end 17 of the fiber and the emitted signal is returned along the fiber and through the indicator-containing cells to an appropriate monitor which interprets the signal to give an indication of the pH of the medium around the distal portion of the catheter. An optical fiber sensor having an embedded mirror is described and claimed in commonly assigned U.S. patent application Ser. No. 887,457 (U.S. Pat. No. 5,257,338)

FIG. 3 illustrates a preferred $pCO_2$ sensor 8 which comprises an optical fiber 18 having an array of cells 19 which substantially covers the cross-sectional area of the fiber and a mirror 20 embedded close to the distal end 21. These features are similar to those in the pH sensor described above. However, the preferred number of cells in the $pCO_2$ sensor is three and each of these cells is filled with an appropriate indicator, preferably phenol red, in a solution which is a source of bicarbonate ions. Preferably the solution is sodium carbonate which is converted to the bicarbonate after incubation. The sensor is enveloped by a tubular membrane 22 of carbon dioxide-permeable polymer, preferably polyethylene.

FIG. 4 illustrates an electrochemical $pO_2$ sensor 10 comprising two elongate insulated conductors 23,24, each having a stripped distal portion, the exposed metal of which provides an active surface forming an anode 25 and cathode 26, respectively. Preferably the anode has a longer active surface than the cathode. In the embodiment illustrated in FIG. 4 the insulated conductor forming the anode is folded into a "U" shape 27 such that the distal end surface of the anode faces the distal end surface of the cathode. The advantage of this configuration is that it reduces or eliminates the consumption of uninsulated metal from the active surface of the electrodes other than the distal end thereof, which was a problem frequently encountered in prior art electrochemical cells. An electrochemical $pO_2$ sensor such as that illustrated in FIG. 4 is described and claimed in commonly assigned U.S. patent application Ser. No. 07/887,615 (U.S. Pat. No. 5,262,037). An alternative embodiment (not illustrated) which overcomes the above described problem is an electrochemical cell in which the electrodes are aligned in substantially parallel relationship alongside each other, again with the active surface of the anode being longer than the active surface of the cathode, and wherein the insulated portion of the conductor is covered or coated with an additional layer of insulation. This double insulation prevents short-circuiting caused by pinholes or other defects in the original (single layer) insulation.

In the preferred embodiment the anode and cathode are made of silver wire. Other conductors, such as platinum may be used.

The anode and cathode are contained within a compartment 28 defined by an oxygen gas permeable membrane 29 that permits oxygen to diffuse therethrough. The distal end of the compartment is sealed with a plug 30 made from a thermoplastic polymer. The gap 31 between the anode and the cathode, as well as the rest of the compartment surrounding the electrodes, is filled with an electrolyte, for example a buffered potassium chloride aqueous solution. The electrochemical cell formed by the anode, cathode and electrolyte is an oxygen sensor whereby concentration of oxygen in the surrounding medium, for example, blood, is measured by changes in electric current flow across the gap 31. The current is generated from a source (not shown) connected across the proximal ends of the conductors and changes are measured by a current measuring device in circuit with the source.

Figure 5:
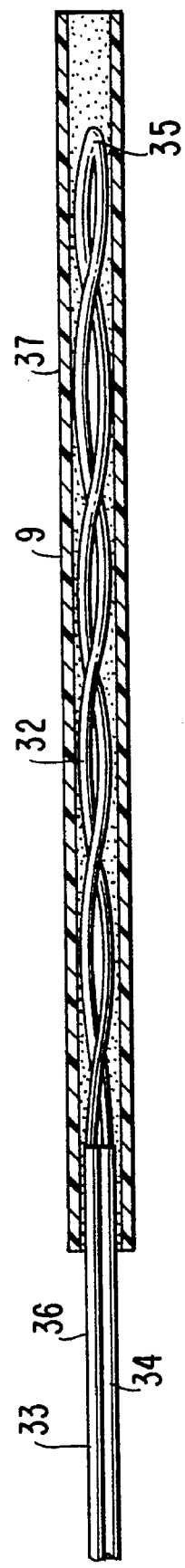
FIG. 5 is an enlarged side view of a thermocouple included in the catheter of FIG. 1.

FIG. 5 illustrates a temperature sensor 9 which comprises a thermocouple formed from the stripped distal portion 32 of two insulated metal wires 33, 34. The distal ends of the wires are welded together to form a welded tip. Preferably the wires are 0.05 mm. copper wire and 0.05 mm. copper/nickel alloy wire and both wires are insulated with a polyurethane coating 36. The stripped portion of the wires is enveloped by a plastic sleeve 37. The thermocouple temperature sensor is a conventional device in the art.

Figure 6:
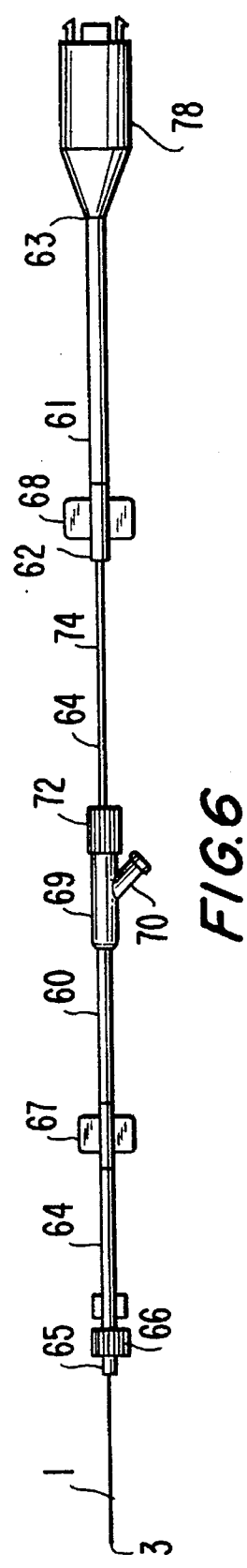
FIG. 6 is a schematic side view of a preferred device for introducing a catheter of FIG. 1 into a patient's blood vessel.

The multi-parameter catheter described above and illustrated in FIG. 1 of the drawings is adapted to be introduced into a blood vessel of a patient, through a cannula previously inserted in the vessel, with the aid of an introducer device such as that illustrated in FIG. 6 of the drawings.

FIG. 6 schematically illustrates an apparatus comprising the combination of a catheter 1 and an introducer device 60.

The introducer comprises a first elongated flexible hollow tube 61 having a distal end 62 and a proximal end 63, and a second elongated extension tube 64. The second tube has an outer diameter the same as or slightly less than the inner diameter of the first tube, and the second tube is concentrically mounted within a distal portion of the first tube so that it may be telescopically extended beyond the distal end of the first tube or retracted within the distal portion of the first tube. The various positions of the extension tube relative to the catheter are illustrated in FIGS. 6A–6D.

The introducer also comprises, at its distal end, a male luer nozzle 65 associated with a rotatable locking collar 66. The luer is adapted to connect the distal end of the introducer to a tonometer (not shown) in which the sensor-containing distal portion of the catheter is stored and calibrated prior to use. The introducer is locked to the tonometer by tightening the collar 66 and released from the tonometer by loosening the collar.

The introducer further comprises a slidable wing 67 mounted on the extension tube. The slidable wing enables the device to be securely attached to the body of the patient, preferably by taping, after the catheter is properly introduced into a blood vessel. A similar wing 68, which may be fixed or slidable, is mounted on the first tube for a similar purpose.

Located along the second tube and concentrically fixed thereto is a Y junction 69 having an angled port or outwardly extending arm 70 which terminates in an obturator 71. The obturator is adapted to be connected to a source from which sterile liquid may be introduced into the second tube to surround the catheter when it is within the tube. Sterile liquid is introduced to flush the system and remove air bubbles. Also, the angled port may be used for taking blood samples or monitoring blood pressure. Thus the extension tube and the associated Y junction make it easier to access the proximal portion of the catheter away from the site of insertion. A cannula protects the site of entry of the catheter into a blood vessel, usually the radial or femoral artery. A clamp nut 72 which threadably tightens the Y junction about the second tube through an O-ring 73 (see FIG. 6D) also acts as a locking means for locking the second tube relative to the first tube. The clamp nut has to be loosened to enable the second tube to be moved telescopically with respect to the first tube.

When the second tube is in a fully extended or partially extended position relative to the first tube, as indicated, for example, in FIG. 6, and FIGS. 6A, 6B and 6D, a portion 74 of the second tube between the clamp nut end the distal end 62 of the first tube is exposed and this exposed portion preferably has gradations, preferably in cm., to enable the operator to determine the depth of penetration when the catheter is inserted in a patient's blood vessel. Also located on the exposed portion of the second tube is a removable stop 75 which facilitates positioning of the catheter when it is inserted in a patient's radial artery. As shown in the cross-sectional view of FIG. 6D, leads 76 from the sensors in the catheter, both optical fibers and metal conductors, are connected to terminals 77, i.e. sockets and ferrules, in a connector 78. The junction formed by the connector 78 and a cooperating connector (not shown) leading to a monitor for determining the parameters under investigation by the sensors is described in U.S. Pat. No. 5,230,031.

FIG. 6 and FIG. 6D show the relative positions of the introducer 64 and the catheter 1 when the catheter is still in the tonometer (not shown). The catheter is maintained in a sterile environment in the tonometer, which is packaged in a sterile package, such as that described in U.S. patent application Ser. No. 07/888,569 (U.S. Pat. No. 5,246,109), prior to use. When the catheter is to be used it is first calibrated while being retained in the tonometer. After calibration the collar 66 and the clamp nut are loosened so that the tonometer may be removed and the second tube be extended forward to envelop the distal portion of the catheter at the position illustrated in FIG. 6A. Sterile liquid introduced through obturator 71 and line 70 flushes out tonometer solution, removes air bubbles, maintains a sterile environment around the catheter and prevents contamination from atmospheric contaminants. Also, immediately prior to use heparinized saline solution is introduced to prevent clot formation. The apparatus may be locked in this position with the catheter retracted inside the introducer by tightening the clamp nut 72. When the catheter is to be introduced into a patient's blood vessel, the nozzle is placed within a cannula, previously inserted into the blood vessel, the clamp nut is loosened and the second tube is retracted back into the first tube thereby allowing the catheter to be threaded into the cannula. When the removable stop 75 is placed at a predetermined distance along the second tube and the catheter is inserted to a depth so that the stop rests against the distal end of the first tube as shown in FIG. 6B this is typically the proper depth for the radial artery position. When the stop is removed and the second tube is retracted so that the end of the clamp nut comes to rest against the distal end of the first tube, as shown in FIG. 6C, this is typically the femoral artery position. Alternatively, since patients are of different sizes the operator may determine the proper depth of insertion by using the gradations 74 on the second tube. When the catheter is inserted to the proper position, the clamp nut is tightened, thus locking the catheter, second tube and first tube and the apparatus is strapped to the arm or leg of the patient with the aid of the wings 67, 68.

In summary, the apparatus comprising the combination of catheter and introducer facilitates the introduction of the catheter into a blood vessel through a cannula whilst minimizing contamination by physical contact. The main parts of the introducer are:

(i) The extension tube (second tube) which allows the fixing of various clinical tubing fittings to be distal from the site of cannulation.

(ii) The Y junction compression fitting which allows reversible hermetic sealing around the catheter. The Y junction also allows the attachment of pressure lines, blood sampling lines and other accessories.

(iii) The concentric first and second tubes allow the advancement of the catheter by sliding of the second tube attached to the catheter relative to the first whilst keeping the catheter completely covered. Thus, when in the advanced position, no portion of the catheter in contact with body fluids can have been contaminated by physical contact with outside contaminants.

The multi-parameter catheter included in the apparatus has the various features and components described above. In particular, at least a part of the outer wall or sheath of the catheter is defined by a biphasic membrane according to the invention, the space surrounding the sensors within the catheter is filled with a hydrophilic medium, and the cells in the optical fiber sensors are filled with an indicator-containing medium. Filling of the micropores of the biphasic membrane and the other filling operations described herein are achieved with the aid of a vacuum rig apparatus as illustrated in FIG. 7 and 8 of the drawings.

Figure 7:
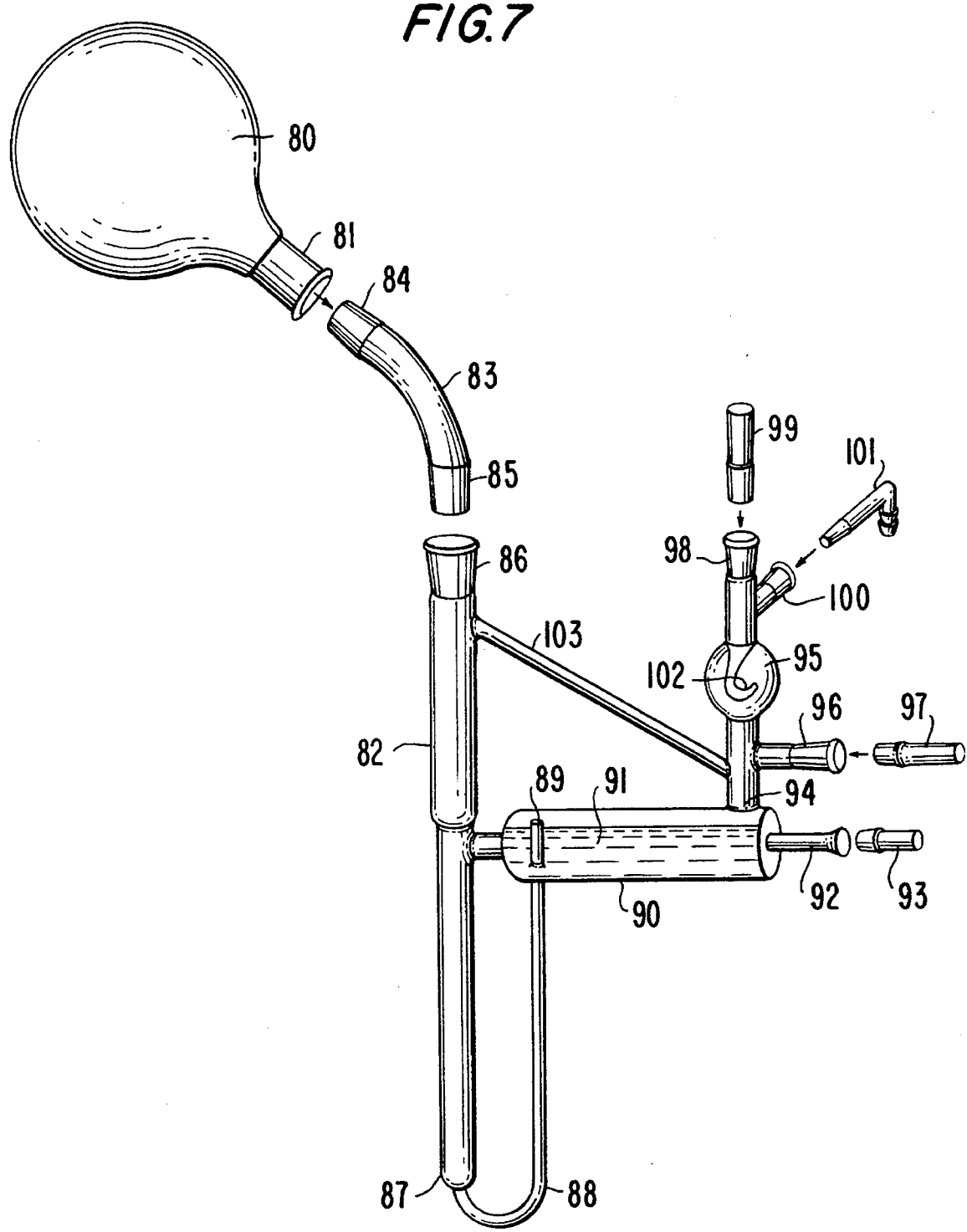
FIG. 7 is a schematic panoramic view of a vacuum rig apparatus.
Figure 8:
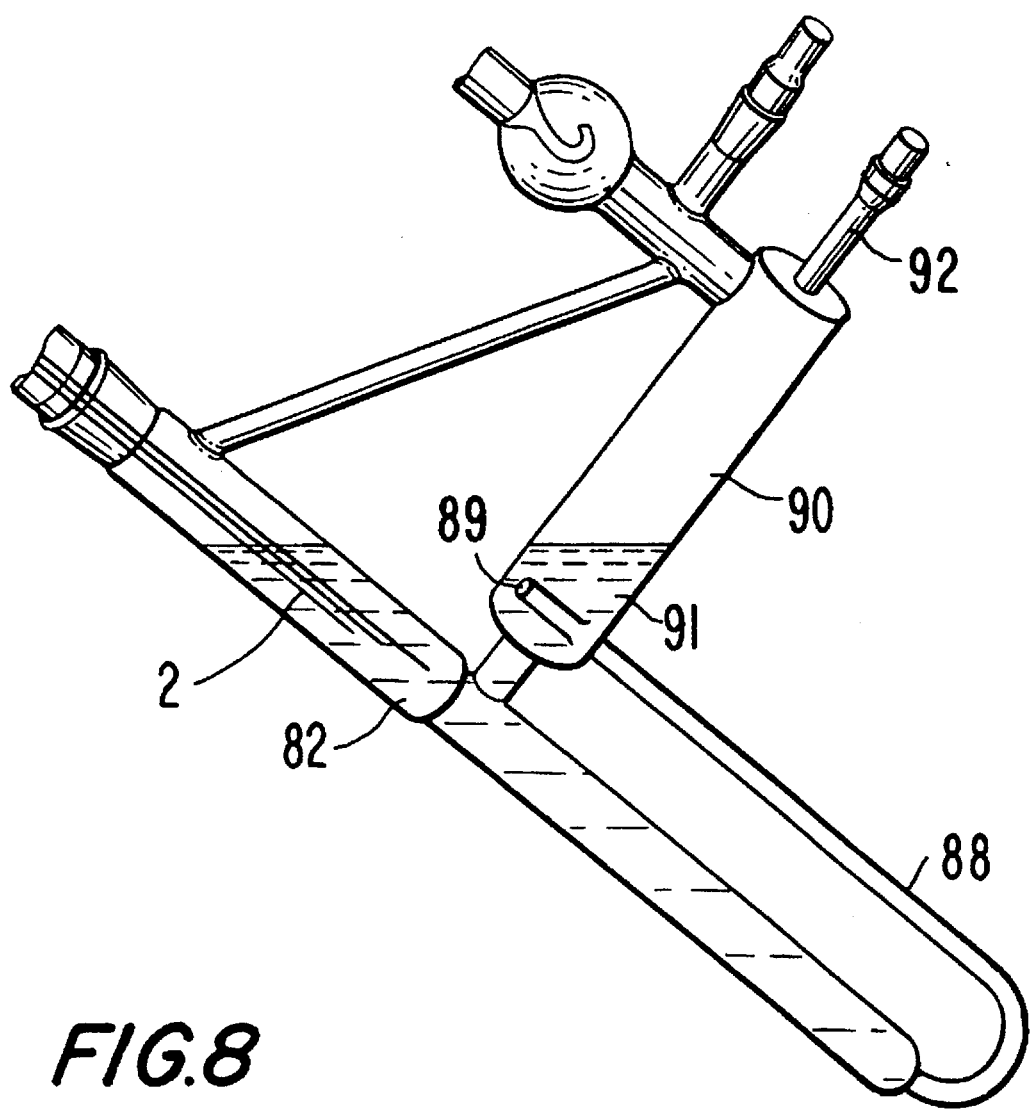
FIG. 8 is a view of part of the vacuum rig apparatus in the tilted position.

The apparatus illustrated in FIG. 7 comprises a first vessel 80, which in the preferred embodiment is a spherical bottle, made of glass or transparent plastic, having an exit port 81 enabling it to be connected to a second vessel 82. In the preferred embodiment the connection between the first vessel and the second vessel is a tubular conduit 83 having an arc-shaped profile and tapered ends 84, 85 which make a fluid-tight connection with a female port 81 in the first vessel and a female port 86 in the second vessel, respectively. The second vessel is a hollow tube having a proximal end terminating in the port 86 and a distal end 87 which is integral with a "U" shaped tube 88 having an open distal end 89 which projects into a space defined by a third vessel 90. In the preferred embodiment the third vessel is substantially tubular in shape and the tube is perpendicular to the tubular second vessel. The tubular third vessel is a reservoir for liquid and when the apparatus is used as described hereinafter liquid 91 is introduced into the reservoir up to a level just below the distal end 89 of the "U" tube. The distal end of the reservoir has a first port 92 which acts as a drain and is sealed with a liquid-tight plug 93 when the apparatus is in use. The reservoir also has a second port 94 through which it is connected to a fourth vessel 95. The fourth vessel has a first port 96 which acts as an additional drain and may be sealed with a plug 97; a second port 98 through which liquid is introduced into the apparatus and which is sealed with a plug 99; and a third port 100 which is adapted to be connected to a vacuum line 101 through which a vacuum may be pulled on the apparatus. A hook shaped trap 102 is located at the lower end of the entry port 98. This trap prevents liquid from being sucked back into the vacuum line when a vacuum is pulled. A tubular conduit 103 connects the second vessel to the fourth vessel and acts as a vent when a vacuum is pulled on the apparatus.

The vacuum rig apparatus is used for introducing a liquid into a space defined by a shaped article. Shaped articles of particular interest herein, all of which may be filled with the desired liquid medium by the vacuum rig apparatus of the invention, are the optical fiber pH and $pCO_2$ sensors (where the liquid medium is a solution of gel and indicator), and the electrochemical $pO_2$ sensor (where the liquid medium is an electrolyte solution), used in the multi-parameter catheter described herein, the catheter itself and the biphasic membrane of the invention. For the purpose of illustration the operation of the vacuum rig apparatus will be described with reference to microporous hollow fibre (MPHF) used to form the biphasic membrane of the invention. A bundle of MPHF, for example microporous polyethylene having a porosity of 40%, is placed in the first vessel 80 of the apparatus in the upright position as shown in FIG. 7 so that the distal end 2 containing the micropores to be filled with liquid extend into and are suspended within the second vessel 82, as shown in FIG. 8. The ports 92 and 96 are sealed with plugs 93 and 97, respectively, and the reservoir 90 is filled, through port 98, with the desired liquid 91, for example, a gelling solution containing polyacrylamide, indicator and gelling agent, up to a level just below the distal end 89 of the "U" tube. The entry port 98 is then sealed with plug 99 and, with the apparatus still in the upright position, a vacuum is pulled on the apparatus through line 101 and port 100. The vacuum is maintained until the liquid is fully degassed and the micropores in the MPHF are evacuated, usually about 15–20 minutes. The rig is then tilted to the position shown in FIG. 8 whereupon the liquid 91 from the reservoir enters the distal end 89 of the "U" tube and runs down the tube 88 and into the second vessel 82 where it surrounds the fibers and diffuses into the evacuated micropores, thus providing a hydrophilic infrastructure within a hydrophobic matrix.

The following working example illustrates in more detail the preparation of hydrophilic gel filled porous fibers according to the invention.

EXAMPLE

(A) Vacuum Filling Ethanol/Water

A 60/40 v/v solution of ethanol and ultra high purity (UHP) water was prepared by mixing 60 ml. of ethanol and 40 ml. of water in a 100 ml. measuring cylinder. The solution was poured into the reservoir of a vacuum rig as described herein. A bundle of sensors (about 50), bound with polytetrafluoroethylene (PTFE) tape was loaded into the vacuum rig so that the distal ends of the sensors extended into the sensor-holding vessel 82. The entry port of the vacuum rig was sealed and the vacuum line connected to the vacuum port. The vacuum line was opened, while ensuring that the needle valve inlet was closed, and a vacuum was pulled until a vacuum of 0–10 mbar was reached. The vacuum was held on the solution until the liquid was fully degassed, about 15–20 minutes.

The vacuum rig was then tilted (FIG. 8) so that the solution poured into the sensor-holding vessel and fully covered the complete length of the MPHF on all the sensors plus about 10–20 mm. above the butt-joint between the tubing 6 and the sheath 2 (FIG. 1). The rig was then returned to the upright position and the sensors immersed in ethanol for a further 5 minutes. The vacuum line was closed, the inlet valve fully opened and the interior of the rig allowed to reach atmospheric pressure.

(B) Gelling Solution (Diffusion Fill)

Because of the hazardous nature of the solution used in this step the handler should wear protective clothing, including gloves, goggles and face mask.

A 250 ml. flask is filled with a gelling solution comprising 15% w/w acrylamide monomer, 2.65% w/w methylene bisacrylamide cross-linking agent, 7.65% w/w ammonium persulphate initiator, and 12% w/w indicator (for example, phenol red) in a phosphate buffered aqueous solution adjusted to pH 3 with hydrochloric acid, and the solution was stirred with an ultrasonic stirrer. The sensors, treated in step (A) above were now transferred from the vacuum rig. Since the ethanol/water mixture is volatile and the sensors can dry out very quickly, the sensors were transferred to a vessel containing UHP water. The sensors were immersed in the gelling solution such that the full length of the MPHF was submerged, and the sensors were held in the gelling solution for two hours.

(C) Set Gel

Again protective clothing should be worn by the handler.

A heated water bath was switched on until the temperature reached 40°±1° C., the temperature being checked with a thermometer. A number of test tubes were filled with a solution of TMED (N,N,N',N'-tetramethylethylene diamine), and placed in holders in the water bath.

The sensors were removed individually from the gelling solution and each sensor was dipped into an individual test tube containing TMED solution for four minutes, ensuring that the MPHF portion of the sensor was fully immersed in the TMED solution. Each of the sensors was then removed from the TMED solution and transferred directly into an acid conditioning solution of about 17% w/v sodium dihydrogen orthophosphate at a pH of 4.5 and held in the solution for about 30 minutes. When all of the gelled portions of the sensors were a solid yellow color they were ready for transfer to the cure bath.

(D) Curing

The sensors were removed individually from the acid conditioning solution. A hanger was attached to the tip of each sensor and the sensors were racked with the MPHF portion fully submerged in the tonometer solution, i.e. a 12 m/M molar solution of sodium carbonate and sodium sulphate. During this operation the circulation system is run constantly to ensure that there was no microbiological contamination of the cure bath.

The temperature of the cure bath was set to 50°–55° C. and maintained at this temperature for not less than 2 hours.

The cured sensor was mounted in a tonometer which was then sealed in a package where it was sterilized and stored until required for use.

We claim:

1. A multi-parameter catheter for the in vivo determination of multiple parameters in a patient's blood comprising an elongated tube with a distal hollow chamber having a wall terminating in a distal end, the wall of said chamber being defined at least in part by a biphasic membrane which is a microporous polyethylene tube having micropores which are filled with a polyacrylamide hydrogel which allows the passage of water-bound ions, said chamber containing a plurality of sensors mounted sequentially from said distal end within a polyacrylamide hydrogel, the sequentially mounted sensors comprising, in sequence from the distal end of the chamber, an optical fiber pH sensor, an optical fiber $pCO_2$ sensor, a thermocouple temperature sensor and a $pO_2$ sensor, and the distal end of the chamber being sealed by a solid plug made from a thermoplastic polymer.

2. A catheter according to claim 1, in which the biphasic membrane has a proximal end which forms a butt-joint with a sheath of non-porous polymeric tubing which covers a proximal portion of the catheter.

3. A catheter according to claim 2, in which a proximal portion of the catheter is back-filled with a radiation-opaque coating over the non-porous polymeric tubing.

4. An apparatus for the in vivo determination of multiple parameters in a patient's blood comprising, in combination, a catheter according to claim 5 and a device for introducing said catheter into a patient's blood vessel, said device comprising a first elongated flexible hollow tube having a distal end, a proximal end and a distal portion terminating in said distal end, a second elongated extension tube having a distal end and a proximal end concentrically mounted within the distal portion of said first tube for telescopic extension beyond the distal end of said first tube and retraction within said first tube, so that when the second tube is fully extended it completely envelopes the catheter and when it is retracted the catheter is exposed, the device also including locking means for locking the second tube in the extended or retracted position as desired and means for introducing a sterile liquid within said second tube to surround the catheter when it is within the tube.

5. An apparatus according to claim 4, in which the introducer device has a connector at the proximal end thereof, which connector is attached to leads from each sensor of the catheter.

6. An apparatus according to claim 4, which includes a tonometer for storing and calibrating the sensor-containing catheter prior to use, which tonometer is attached to the distal end of the introducer device through a male luer lock with a rotatable collar, the said catheter being in the extended position beyond the distal end of the second tube of the introducer device for accommodation within the tonometer.

7. An apparatus according to claim 4, in which the means for introducing a sterile liquid within the second tube is a Y-junction mounted on the second tube at a position adjacent a proximal end of the catheter when the catheter is fully retracted, one arm of the Y extending outwardly from the second tube and terminating in a male luer lock obturator capable of being attached to a source of sterile liquid for introduction into the second tube and the other arm of the Y lying coaxially along the second tube and terminating proximally in a rotatable clamp nut which provides the locking means for locking the second tube in a desired position relative to the first tube and sealing the second tube around the catheter.

8. An apparatus according to claim 4 which includes means for securing the catheter against the body of the patient.

* * * * *